United States Patent [19]

Bott et al.

[11] Patent Number: 4,939,268

[45] Date of Patent: Jul. 3, 1990

[54] 4-((METH)ACRYLAMIDOMETHYL)-PYRAZOLES AND -ISOXAZOLES, THEIR PREPARATION AND THEIR USE

[75] Inventors: Kaspar Bott, Mannheim; Bernhard Nick, Ludwigshafen; Guenther Schulz, Bad Durkheim, all of Fed. Rep. of Germany

[73] Assignee: BASF Aktiengesellschaft, Fed. Rep. of Germany

[21] Appl. No.: 360,987

[22] Filed: Jun. 2, 1989

[30] Foreign Application Priority Data

Jun. 8, 1988 [DE] Fed. Rep. of Germany ....... 3819456

[51] Int. Cl.$^5$ .................. C07D 231/12; C07D 261/08
[52] U.S. Cl. ..................................... 548/247; 548/378
[58] Field of Search ................................ 548/247, 378

[56] References Cited

FOREIGN PATENT DOCUMENTS 0188037 7/1986 European Pat. Off. .

*Primary Examiner*—Anton H. Sutto
*Assistant Examiner*—Edward Rosfjord

*Attorney, Agent, or Firm*—Keil & Weinkauf

[57] ABSTRACT

Novel 4-[(meth)acrylamidomethyl]-pyrazoles and -isoxazoles of the general formula

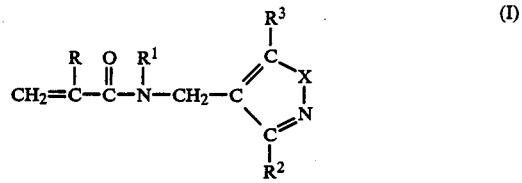

where R is hydrogen or methyl, $R^1$ is hydrogen, methyl or ethyl, $R^2$ and $R^3$ may be identical or different and are each alkyl of 1 to 6 carbon atoms or unsubstituted or substituted aryl of 6 to 20 carbon atoms, and X is oxygen or an $NR^4$ group where $R^4$ is hydrogen or a radical having the meanings of $R^2$ or $R^3$, a process for their preparation, and the use of these compounds in particular for polymerization and the preparation of homopolymers and copolymers, are described.

8 Claims, No Drawings

4-((METH)ACRYLAMIDOMETHYL)-PYRAZOLES AND -ISOXAZOLES, THEIR PREPARATION AND THEIR USE

The present invention relates to novel 4-[(meth)acrylamidomethyl]-pyrazoles and -isoxazoles.

The present invention furthermore relates to a process for the preparation of these compounds and novel homopolymers and copolymers prepared using these compounds.

Compounds which contain a heterocyclic group and an olefinically unsaturated radical capable of undergoing polymerization have long been known. Typical examples of these are vinylpyridine, N-vinylpyrrolidone and N-vinylcarbazole. They can readily be converted into homopolymers or copolymers which, although they have a wide range of applications, do not always meet all requirements in some fields of use, for example in the area of photosensitive offset printing plates or surface coatings.

In the area of surface coatings, the compounds which are disclosed in No. EP-A-188 037 and in which a heterocyclic group is bonded to a (meth)acrylic acid radical have resulted in a certain amount of progress. Typical examples of the compounds described in No. EP-A-188 037 are

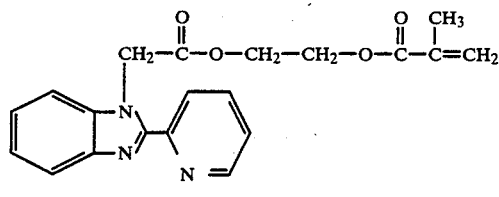

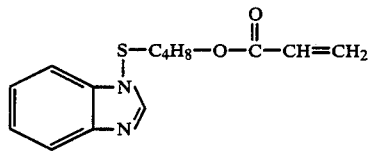

or

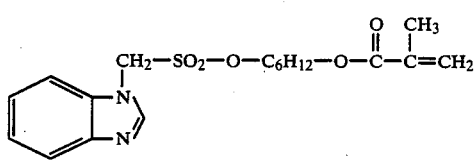

In these known compounds, the heterocyclic group is bonded to the (meth)acryloyl radical via one or two ester functions. The use of the homopolymers and copolymers prepared therefrom in the area of photosensitive offset printing plates is not evident from No. EP-A-88 037.

Apart from this, these compounds have the disadvantage that the ester functions present therein are readily hydrolyzable. Hence, the compounds decompose in the presence of water, aqueous alkaline solutions, ammonia or amines. They are therefore suitable only for applications in which there is no danger of decomposition and the associated loss of the typical properties. Morever, many synthesis steps are required in the preparation of these compounds in order to achieve bonding of the heterocyclic group to the (meth)acryloyl radical, further reducing the attractiveness of these compounds.

It is an object of the present invention to provide novel, stable compounds which are simple to prepare and in which a heterocyclic group is bonded to a radical containing an olefinic double bond which can be subjected to free radical polymerization, the said compounds not having the disadvantages of the prior art.

We have found, surprisingly, that this object is achieved by 4-[(meth)acrylamidomethyl]-pyrazoles and -isoxazoles of the type defined and described below.

The present invention accordingly relates to 4-[(meth)acrylamidomethyl]-pyrazoles and -isoxazoles of the general formula (I)

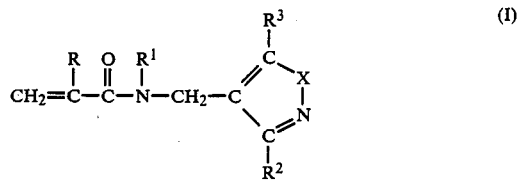

where R, $R^1$, $R^2$, $R^3$ and X independently of one another have the following meanings: R is hydrogen or methyl, preferably hydrogen, $R^1$ is hydrogen, methyl or ethyl, preferably hydrogen, $R^2$ and $R^3$ may be identical or different and are each alkyl of 1 to 6 carbon atoms or aryl of 6 to 20 carbon atoms which is unsubstituted or substituted by, for example, alkyl, aryl or halogen, and X is oxygen or an $NR^4$ group, where $R^4$ is hydrogen or a radical having the meanings of $R^2$ or $R^3$.

Examples of the radicals $R^2$ and $R^3$ in the general formula (I) are methyl, ethyl, n-propyl, isopropyl, n-butyl, sec-butyl, tert-butyl, pent-1-, -2- or -3-yl and hex-1-, -2- or -3-yl, and furthermore phenyl, 2-, 3- and 4-methylphenyl, 2,4-dimethylphenyl, 4-tert-butyl-, 4-chloro- and 4-bromophenyl, 4-phenylphen-1-yl (biphenylyl), 4-(4,-phenylphen-l,-yl)-phen-1-yl (triphenylyl), 1- and 2-naphthyl, phenanthren-7-yl, anthracen-1-yl, fluoren-2-yl and perylen-3-yl. Of these radicals, methyl, ethyl, n-propyl and phenyl are preferred according to the invention, methyl and phenyl being very particularly preferred.

Examples of $R^4$ are the groups stated above for $R^2$ and $R^3$. $R^4$ is preferably hydrogen, methyl, ethyl, n-propyl or phenyl, in particular hydrogen or phenyl.

Examples of preferred novel 4-[(meth)acrylamidomethyl]-pyrazoles and -isoxazoles of the general formula (I) are

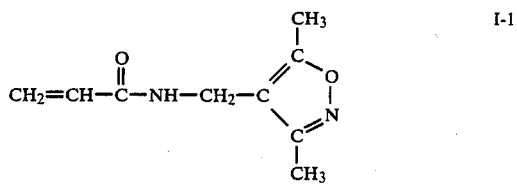

I-1

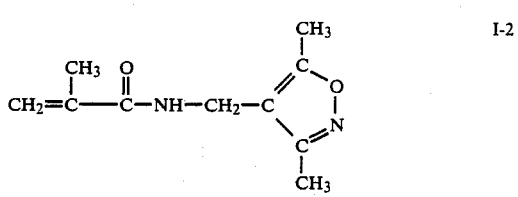

I-2

-continued

I-3 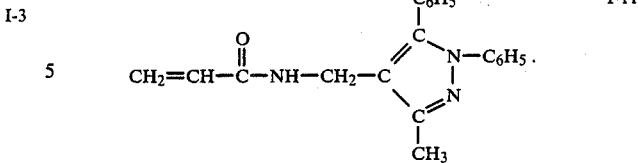

I-4 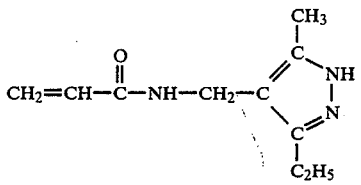

I-5 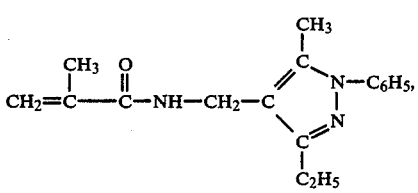

I-6 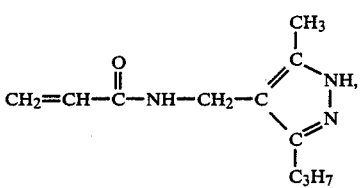

I-7 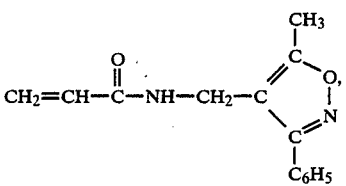

I-8 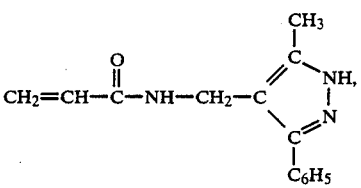

I-9 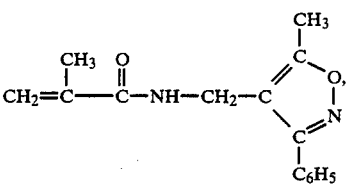

I-10 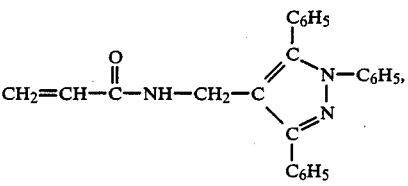

I-11 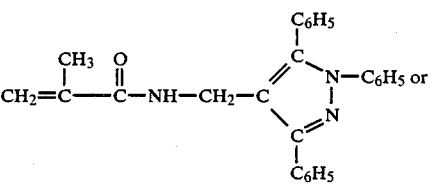

Of these, the compounds I-6 [3-phenyl-4-(acrylamidomethyl)-5-methylisoxazole], I-7 [3-phenyl-4-(acrylamidomethyl)-5-methylpyrazole], I-9 [1,3,5-triphenyl-4-(acrylamidomethyl)-pyrazole] and I-11 [1,5-diphenyl-3-methyl-4-(acrylamidomethyl)-pyrazole] are very particularly preferred.

The novel 4-[(meth)acrylamidomethyl]-pyrazoles and -isoxazoles of the general formula (I) can be prepared by conventional and known methods of preparative organic chemistry. However, it is advantageous to prepare the novel 4-[(meth)acrylamidomethyl]-pyrazoles and -isoxazoles of the general formula (I) by a novel procedure, by condensation of a suitable 1,3-diketone with (a) a hydrazine or with (b) a hydroxylamine.

This novel process starts from a 1,3-diketone of the general formula (II)

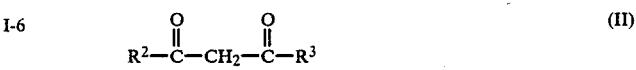  (II)

where $R^2$ and $R^3$ may be identical or different and independently of one another are each alkyl of 1 to 6 carbon atoms or unsubstituted or substituted aryl of 6 to 20 carbon atoms. Examples of the radicals $R^2$ and $R^3$ in the general formula (II) are the radicals stated for $R^2$ and $R^3$ in the general formula (I). Of these radicals, methyl, ethyl, n-propyl and phenyl are particularly preferred according to the invention, methyl and phenyl being very particularly preferred.

Examples of 1,3-diketones of the general formula (II) which are very particularly preferably used in the novel process are pentane-2,4-dione (II-1), benzoylacetone (II-2) and 1,3-diphenylpropane-1,3-dione (II-3).

In the novel procedure, the 1,3-diketones of the general formula (III) are dissolved or dispersed in a sufficient amount of a strong acid as a reaction medium at from −5° to +10° C., in particular at about 0° C. A suitable amount of acid is in general about from 2 to 20 times, the weight of the 1,3-diketone of the general formula (II). Suitable strong acids include concentrated sulfuric acid, concentrated phosphoric acid and concentrated trifluoromethanesulfonic acid, of which the first-mentioned is particularly advantageous.

An equimolar amount of an N-methylol(meth)acrylamide of the general formula (III)

  (III)

where R is hydrogen or methyl and, independently of this, $R^1$ is hydrogen, methyl or ethyl, is then added to this solution or dispersion of the 1,3-diketone of the general formula (II). According to the invention, N-methylol(meth)acrylamides of the general formula (III) where $R^1$ is hydrogen are preferred here. N-methylolacrylamide is very particularly preferred. It is known that the N-methylol(meth)acrylamides of the general formula (III) can be prepared in a simple manner from formaldehyde and the corresponding (meth)acrylamide.

According to the invention, it is advantageous to add a conventional and known thermal polymerization inhibitor to the resulting reaction mixture. Examples of suitable polymerization inhibitors are trisnonylphenyl phosphite, 2,6-di-tert-butyl-p-cresol, hydroquinone monomethyl ether and polymerized trimethyldihydroquinone, of which hydroquinone monomethyl ether is particularly advantageous. The polymerization inhibitors are added to the reaction mixture in amounts of from 0.001 to 5% by weight, based on the N-methylol(-meth)acrylamide of the general formula (III).

The resulting reaction mixture of the 1,3-diketone of the general formula (II), the N-methylol(meth)acrylamide of the general formula (III), the strong acid and, if required, the polymerization inhibitor is then stirred at from 15° to 40° C., preferably from 15° to 0° C., in particular from 20° to 25° C., for from 1 to 48, preferably from 2 to 40, in particular from 2.5 to 20, hours. During this time, the condensation reaction takes place between the 1,3-diketone of the general formula (II) and the N-methylol(meth)acrylamide of the general formula (III) to give the relevant 2-[(meth)acrylamidomethyl]-1,3-diketone of the general formula (IV).

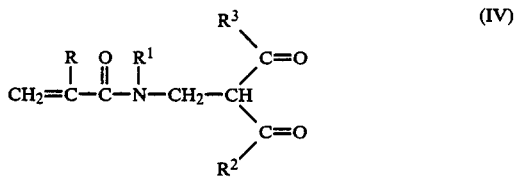

(IV)

In the general formula (IV), R, $R^1$, $R^2$ and $R^3$ have the meanings stated above for these radicals in connection with the general formulae (II) and (III).

The reacted mixture is then poured onto a large excess of, preferably crushed, ice, with the result that the relevant 2-[(meth)acrylamidomethyl]-1,3-diketone of the general formula (IV) is precipitated. The precipitate and any product still present in the aqueous phase are then extracted with an organic solvent, for example toluene, xylene or a halohydrocarbon, such as dichloromethane, the solvent is evaporated off and the residue is then recrystallized from a suitable solvent or solvent mixture.

For the preparation of the novel 4-[(meth)acrylamidomethyl]-pyrazoles of the general formula (I), the 2[(meth)acrylamidomethyl]-1,3-diketones of the general formula (IV) are condensed with a preferably equimolar amount of a hydrazine by the novel process.

Examples of suitable hydrazines to be used according to the invention are hydrazinium salts, such as hydrazinium fluoride, chloride, bromide, bisulfate, dihydrogenphosphate and trifluoromethanesulfonate, of which hydrazinium bisulfate is preferably used. Other examples of suitable hydrazines are hydrazine derivatives of the general formula (V)

$NH_2-NH-R^4$ (V)

where $R^4$ is one of the radicals $R^2$ or $R^3$ described above. Of these hydrazine derivatives of the general formula (V), phenylhydrazine is preferably used.

For the preparation of the novel 4-[(meth)acrylamidomethyl]-isoxazoles of the general formula (I), the 2-[(meth)acrylamidomethyl]-1,3-diketones of the general formula (IV) are condensed with a preferably equimolar amount of hydroxylamine, preferably a hydroxylammonium salt, by the novel process. Examples of hydroxylammonium salts which are preferably used according to the invention are hydroxylammonium fluoride, chloride, bromide, bisulfate, dihydrogenphosphate and trifluoromethanesulfonate, of which hydroxylammonium chloride is particularly preferably used.

Regardless of whether the novel 4-[(meth)acrylamidomethyl]-pyrazoles of the general formula (I) or the novel 4-[(meth)acrylamidomethyl]-isoxazoles of the general formula (I) are produced from the 2-[(meth)acrylamidomethyl]-1,3-diketones of the general formula (IV) in the novel process, the relevant condensation of the 1,3-diketones of the general formula (IV) with the hydrazines or the hydroxylamines is carried out in an aqueous reaction medium. For the purposes of the present invention, an aqueous reaction medium is water which contains dissolved or dispersed organic and/or inorganic additives.

Examples of suitable additives which are present in the aqueous reaction medium include carboxylic acids, such as acetic acid, propionic acid or butyric acid, of which acetic acid is preferred. Other examples of suitable additives of the type under discussion are carboxylic acid salts, such as sodium acetate, potassium acetate, sodium propionate, potassium propionate, sodium butyrate and potassium butyrate, of which sodium acetate is preferably used. Suitable aqueous reaction media contain water and the additives in a weight ratio of water to additives of from 1:5 to 1:1.

Examples of aqueous reaction media preferably used according to the invention are water plus acetic acid in a weight ratio of from 1:5 to 1:1 or water plus acetic acid plus sodium acetate in a weight ratio of from 1:1:0.05 to 1:1:0.2.

The narrower choice of the aqueous reaction medium which is most suitable for the relevant condensation depends in particular on the solubility and/or dispersibility of the reactants in this aqueous reaction medium and can be made on the basis of simple preliminary experiments.

Regardless of the particular aqueous reaction medium in which the novel process is carried out, the condensation reaction is effected either by a procedure in which one of the reactants in the aqueous reaction medium is initially taken and the other reactant is metered in a little at a time or continuously, or by a procedure in which both reactants are dissolved and/or dispersed simultaneously in the relevant aqueous reaction medium. According to the invention, it is advantageous here to add the two reactants simultaneously to the aqueous reaction medium and to carry out the condensation batchwise in a one-vessel process.

Regardless of the manner in which the novel process is carried out, the condensation between the relevant reactants is effected at the boiling point of the aqueous reaction medium, i.e. under reflux. The reaction time after which the condensation reaction has come to an end is usually from 1 minute to 2 hours, in particular about from 2 minutes to 1 hour, preferably about from 3 to 30 minutes. The optimum reaction time for the particular condensation depends on the reactivity of the reactants used in each case and can be determined by preliminary experiments.

After the end of the condensation reaction, the resulting reaction mixture is allowed to cool to room temperature. During this procedure, the novel 4-[(meth)acrylamidomethyl]-pyrazoles or -isoxazoles of the general formula (I) crystallize out, or they are precipitated by diluting the reaction mixture with from two to ten times the amount, based on the reaction mixture, of water.

The products which have crystallized out or have been precipitated are isolated in a conventional and known manner, for example by filtration or centrifuging, and are washed with a suitable organic liquid, e.g. diethyl ether, and/or recrystallized from a suitable solvent or solvent mixture, e.g. methanol, ethanol, isopropanol or ethanol/isopropanol.

The 4-[(meth)acrylamidomethyl]-pyrazoles or -isoxazoles of the general formula (I) obtained in the novel procedure are as a rule then also dried. They can be characterized in a conventional and known manner.

The novel process can be carried out in any glass or metal apparatus of the type conventionally used in the field of preparative organic chemistry.

The novel 4-[(meth)acrylamidomethyl]-pyrazoles and -isoxazoles of the general formula (I), in particular those prepared by the novel process, have particular, advantageous properties and therefore have many potential applications. For example, they are useful intermediates for organic syntheses. In particular, they can be used as polymerizable monomers, in particular monomers which can be subjected to free radical polymerization, preferably photopolymerizable monomers. They are therefore particularly useful for the preparation of novel, photopolymerizable sealing compounds, surface coatings, adhesives and sheet-like recording materials, to which they impart unexpectedly advantageous performance characteristics.

The novel 4-[(meth)acrylamidomethyl]-pyrazoles or -isoxazoles of the general formula (I) are particularly advantageously used for the preparation of homopolymers or copolymers, and, for the preparation of copolymers, the novel pyrazoles or isoxazoles of the general formula (I) can be copolymerized with one another and/or with other conventional monomers. Here, they display the advantageous properties even in the copolymers with other conventional monomers, with the result that these novel copolymers are very suitable, for example, as binders in photosensitive offset printing plates.

Another important advantage of the novel 4-[(meth)acrylamidomethyl]-pyrazoles and -isoxazoles of the general formula (I) is that they can be polymerized or copolymerized by the thermally or photochemically initiated free radical polymerization methods familiar from polymer chemistry. For example, they can be (co)polymerized by mass polymerization, i.e. in the absence of a solvent, or in solution, and the conventional and known free radical initiators, such as organic peroxides, azo compounds, sterically hindered hydrocarbons (C—C initiators), redox initiators or photoinitiators, can be used.

The novel 4-[(meth)acrylamidomethyl]-pyrazoles and -isoxazoles of the general formula (I) can be particularly advantageously copolymerized with the conventional and known monomers from the group consisting of the vinylaromatics, e.g. styrene, α-methylstyrene or p-methylstyrene; nitriles, e.g. acrylonitrile or methacrylonitrile; olefinically unsaturated carboxylic acids and their anhydrides, e.g. (meth)acrylic acid, (meth)acrylic anhydride or maleic anhydride; esters of (meth)acrylic acid, e.g. ethyl (meth)acrylate, 2-hydroxyethyl (meth)acrylate or benzyl acrylate; esters of fumaric or maleic acid, e.g. di-n-butyl or di-n-octyl fumarate or maleate; (meth)acrylamides, e.g. N-hexyl(meth)acrylamide; vinyl ethers, e.g. vinyl butyl ether; vinyl esters, e.g. vinyl acetate or propionate; allyl ethers, e.g allyl butyl ether; allyl esters, e.g. bisallyl itaconate; or alkadienes, e.g. butadiene or isoprene, this list by no means being exhaustive but merely giving typical examples which should be regarded as an indication of other suitable, conventional and known monomers.

Regardless of their intended use and/or of the method by which they are further processed, both the novel 4-[(meth)acrylamidomethyl]-pyrazoles and -isoxazoles of the general formula (I) and the novel (co)polymers prepared therefrom prove to be very stable to hydrolysis. There is therefore no danger of the bond between the heterocyclic group and the (meth)acryloyl radical capable of free radical polymerization or the (co)polymer being cleaved by undesirable side reactions, which would result in a loss of the particularly advantageous properties typical of the novel substances.

EXAMPLES

For the synthesis of the novel 4-[(meth)acrylamidomethyl]-pyrazoles and -isoxazoles, two 2-[(meth)acrylamidomethyl]-1,3-diketones were first prepared (Synthesis Examples I and II).

SYNTHESIS EXAMPLE I

Preparation and characterization of 1-phenyl-2-(acrylamidomethyl)-butane-1,3-dione 1.0 g of hydroquinone monomethyl ether, 100 g of benzoylacetone and 64.8 g of N-methylolacrylamide were introduced one after the other into 500 ml of concentrated sulfuric acid at 0° C. The stirred reaction mixture was left to react at 20° C. for 4 hours, after which it was poured onto 2 kg of crushed ice. The 1-phenyl-2-(acrylamidomethyl)-butane-1,3-dione precipitated during this procedure was dissolved in dichloromethane and the resulting solution was separated off from the aqueous phase. The dichloromethane was then evaporated.

Recrystallization of the product from a mixture of 3 parts by volume of cyclohexane and 1 part by volume of ethanol gave 105 g of 1-phenyl-2-(acrylamidomethyl)-butane-1,3-dione, corresponding to a yield of pure product of 70% by weight, based on the starting materials. The product had a melting point of 125°–126° C.

| Elemental analysis: | C 68.7 | H 6.0 | O 19.7 | N 5.7 |
|---|---|---|---|---|
| Theory: | C 68.56 | H 6.16 | O 19.57 | N 5.71 |

The $^1$H-NMR and IR spectroscopic measurements confirmed the presence of the desired compound.

SYNTHESIS EXAMPLE II

Preparation and characterization of 1,3-diphenyl-2-(acrylamidomethyl)-propane-1,3-dione 1,3-Diphenyl-2-(acrylamidomethyl)-propane-1,3dione was prepared from 143 g of 1,3-diphenylpropane-1,3dione and 64.8 g of N-methylolacrylamide similarly to the method described in Synthesis Example I.

Recrystallization of the product from methanol gave 127 g of 1,3-diphenyl-2-(acrylamidomethyl)-propane-1,3-dione, corresponding to a yield of pure product of 65% by weight. The product had a melting point of 146°–148° C.

| Elemental analysis: | C 74.1 | H 5.6 | O 15.8 | N 4.5 |
|---|---|---|---|---|
| Theory: | C 74.25 | H 5.58 | O 15.62 | N 4.56 |

The $^1$H-NMR and IR spectroscopic measurements confirmed the presence of the desired compound.

EXAMPLE 1

3-Phenyl-4-acrylamidomethyl-5-methylisoxazole

A mixture of 34.6 g of the 1-phenyl-2-(acrylamidomethyl)-butane-1,3-dione prepared according to Synthesis Example I, 9.84 g of hydroxylammonium chloride, 11.6 g of sodium acetate, 180 ml of acetic acid and 180 ml of water was refluxed for 5 minutes, cooled to room temperature and then diluted with 600 ml of water. The crystals precipitated in this procedure were filtered off under suction and washed with diethyl ether. This gave 27.0 g of 3-phenyl-4-acrylamidomethyl-5-methylisoxazole, corresponding to a yield of 79% by weight. The product had a melting point of 149°–151° C.

| Elemental analysis: | C 69.4 | H 5.9 | O 13.1 | N 11.6 |
|---|---|---|---|---|
| Theory: | C 69.41 | H 5.82 | O 13.21 | N 11.56 |

The $^1$H-NMR and IR spectroscopic measurements confirmed the presence of the desired compound.

EXAMPLE 2

3-Phenyl-4-acrylamidomethyl-5-methylpyrazole

A mixture of 29.4 g of the 1-phenyl-2-(acrylamidomethyl)-butane-1,3-dione prepared according to Synthesis Example I, 15.6 g of hydrazinium bisulfate, 19.7 g of sodium acetate, 180 ml of acetic acid and 180 ml of water was refluxed for 5 minutes, cooled to room temperature and then diluted with 600 ml of water. The crystals precipitated in this procedure were filtered off under suction and washed with diethyl ether. This gave 23.1 g of 3-phenyl-4-acrylamidomethyl-5-methylpyrazole, corresponding to a yield of 80% by weight. The product had a melting point of 191°–193° C.

| Elemental analysis: | C 69.4 | H 6.3 | N 17.2 |
|---|---|---|---|
| Theory: | C 69.69 | H 6.27 | N 17.41 |

The $^1$H-NMR and IR spectroscopic measurements confirmed the presence of the desired compound.

EXAMPLE 3

1,3,5-Triphenyl-4-acrylamidomethylpyrazole

A mixture of 67.4 g of the 1,3-diphenyl-2-(acrylamidomethyl)-propane-1,3-dione prepared according to Synthesis Example II, 23.8 g of phenylhydrazine, 230 ml of acetic acid and 50 ml of water was heated at 90° C. for 6 minutes. The product (58.2 g) which crystallized out after cooling to room temperature was recrystallized from ethanol.

The recrystallized product had a melting point of 189°–191° C. The $^1$H-NMR spectroscopic measurement confirmed the presence of 1,3,5-triphenyl-4-acrylamidomethylpyrazole:

$^1$H-NMR (dimethyl sulfoxide; 300 MHz): $\delta=4.20$ (doublet, 2H, —CH$_2$—); $\delta=5.60$ (doublet, 1H, H—C≡C); $\delta=6.15$ (doublet, 1H, H—C≡C); $\delta=6.30$ (double doublet, 1H, H—C≡C); $\delta=7.2$–7.8 (multiplet, 15H, aromatic H); $\delta=8.60$ (triplet, 1H, NH).

EXAMPLE 4

1,5-Diphenyl-3-methyl-4-acrylamidomethylpyrazole

A mixture of 29.4 g of the 1-phenyl-2-(acrylamidomethyl)-butane-1,3-dione prepared according to Synthesis Example I, 12.9 g of phenylhydrazine, 180 ml of acetic acid and 180 ml of water was refluxed for 5 minutes, cooled to room temperature and then diluted with 600 ml of water. The crystals precipitated in this procedure were filtered off under suction and washed with diethyl ether. This gave 37.4 g of 1,5-diphenyl-3-methyl-4-acrylamidomethylpyrazole having a melting point of 157°–159° C. The $^1$H-NMR spectroscopic measurement confirmed the presence of this product:

$^1$H-NMR (dimethyl sulfoxide; 300 MHz): $\delta=2.5$ (singlet, 3H, CH$_3$); $\delta=4.12$ (doublet, 2H, —CH$_2$—); $\delta=5.60$ (doublet, 1H, H—C≡C); $\delta=6.12$ (doublet, 1H, H—C≡C); $\delta=6.25$ (double doublet, 1H, H—C≡C); $\delta=7.10$–7.45 (multiplet, 10H, aromatic H); $\delta=8.30$ (triplet, 1H, NH).

EXAMPLE 5

Preparation of a 3-phenyl-4-acrylamidomethyl-5-methylisoxazole copolymer (i) A solution of 7.5 parts by weight of the 3-phenyl-4-acrylamidomethyl-5-methylisoxazole prepared according to Example 1 in 40 parts by weight of acetone/N-methylpyrrolidone (volume ratio 3:1) and (ii) a solution of 16.3 parts by weight of acrylonitrile, 71.1 parts by weight of ethyl acrylate, 4.3 parts by weight of methacrylic acid and 0.1 part by weight of azobisisobutyronitrile in 3 parts by weight of N-methylpyrrolidone were metered, in the course of 4 hours, into a fournecked flask heated at 60° C. and equipped with a stirrer, an internal thermometer, a dropping funnel and a reflux condenser. The combined solutions were then refluxed for a further hour, while stirring.

Thereafter, (iii) a solution of 2.3 parts by weight of methacrylic acid and 0.1 part by weight of azobisisobutyronitrile in 20 parts by weight of methanol was metered into the reaction solution in the course of one hour, after which the resulting mixture was refluxed for a further hour. Then, (iv) a solution of 1.2 parts by weight of methacrylic acid and 0.1 part by weight of azobisisobutyronitrile in 20 parts by weight of methanol and (v) a solution of 2 parts by weight of azobisisobutyronitrile in 80 parts by weight of methanol were added.

The resulting reaction mixture was then refluxed until the remaining amount of acrylonitrile in the nonvolatile part of the reaction mixture was less than 0.1% by weight (determined by gas chromatography). The copolymer obtained was then isolated by evaporating off the solvent. The copolymer had a Fikentscher K value of 59 (measured in a 1% strength by weight solution of the copolymer in dimethylformamide) and an acid number of 58 mg of KOH/g.

EXAMPLE 6

Preparation of a 3-phenyl-4-acrylamidomethyl-5-methyl preparation of a pyrazole copolymer Example 5 was repeated, except that, instead of the solutions (i) and (ii) used there, solutions of (i) 15 parts by weight of the 3-phenyl-4-acrylamidomethyl-5-methylpyrazole obtained according to Example 2 in 45 parts by weight of methanol and (ii) 13.6 parts by weight of acrylonitrile, 63.6 parts by weight of ethyl acrylate, 4.3 parts by weight of methacrylic acid and 0.1 part by weight of azobisisobutyronitrile in 5 parts by weight of methanol were used, and the combined solutions were refluxed for six hours instead of one hour, after which the other solutions (iii) to (v) were added to the reaction mixture, as stated in Example 5.

The resulting copolymer had a Fikentscher K value of 38.4 and an acid number of 53 mg of KOH/g of copolymer.

EXAMPLE 7

Preparation of a further 3-phenyl-4-acrylamidomethyl-5-methylpyrazole copolymer

Example 5 was repeated, except that, instead of the solutions (i) to (v) used there, the following solutions were employed:

(i) 4.125 parts by weight of the 3-phenyl-4-acrylamidomethyl-5-methylpyrazole obtained according to Example 2 in 18 parts by weight of methanol, (ii) 13.6 parts by weight of acrylonitrile, 71.1 parts by weight of ethyl acryalate, 4.3 parts by weight of methacrylic acid and 0.1 part by weight of azobisisobutyronitrile in 2 parts by weight of methanol, (iii) 2.3 parts by weight of methacrylic acid and 2.25 parts by weight of the 3-phenyl-4-acrylamidomethyl-5-methylpyrazole obtained according to Example 2 in 18 parts by weight of methanol, (iv) 0.1 part by weight of azobisisobutyronitrile in 2 parts by weight of methanol and (v) 1.2 parts by weight of methacrylic acid and 2.25 parts by weight of the 3-phenyl-4-acrylamidomethyl-5-methylpyrazole obtained according to Example 2 in 18 parts by weight of methanol.

Furthermore, a solution of (vi) 0.1 part by weight of azobisisobutyronitrile in 2 parts by weight of methanol and, one hour later, a solution of (vii) 2 parts by weight of azobisisobutyronitrile in 40 parts by weight of methanol were added to the reaction mixture.

The resulting copolymer had a Fikentscher K value of 61.3 and an acid number of 61 mg of KOH/g of copolymer.

The copolymer prepared according to Examples 5, 6 and 7 were very suitable for the production of photosensitive layers of offset printing plates.

We claim:

1. A 4-[(meth)acrylamidomethyl]-pyrazole or -isoxazole of the formula (I)

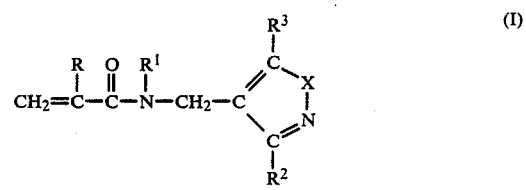

where R, $R^1$, $R^2$, $R^3$ and X independently of one another have the following meanings: R is hydrogen or methyl, $R^1$ is hydrogen, methyl or ethyl, $R^2$ and $R^3$ may be identical or different and are each alkyl of 1 to 6 carbon atoms or unsubstituted or substituted aryl of 6 to 20 carbon atoms and X is oxygen or an $NR^4$ group, where $R^4$ is hydrogen or a radical having the meanings of $R^2$ or $R^3$.

2. A 4-[(meth)acrylamidomethyl]-pyrazole as claimed in claim 1, wherein, in the formula (I), R and $R^1$ are each hydrogen, $R^2$ and $R^3$ are each methyl or phenyl and X is $NR^4$ where $R^4$ is hydrogen or phenyl.

3. A 4-[(meth)acrylamidomethyl]-isoxazole as claimed in claim 1, wherein, in the formula (I), R and $R^1$ are each hydrogen, $R^2$ and $R^3$ are each methyl or phenyl and X is oxygen.

4. A process for the preparation of a 4-[(meth)acrylamidomethyl]-pyrazole or -isoxazole, comprising the following steps: (1) condensing a 1,3-diketone of the formula (II)

where $R^2$ and $R^3$ may be identical or different and independently of one another are each alkyl of 1 to 6 carbon atoms or unsubstituted methyl, t-butyl or phenyl substituted aryl of 6 to 20 carbon atoms, with an N-methylol(meth)acrylamide of the formula (III)

where R is hydrogen or methyl and $R^1$ is hydrogen, methyl or ethyl, in a strong acid as a reaction medium, thereby obtaining a 2-[(meth)acrylamidomethyl]-1,3-diketone of the formula (IV)

$$\begin{array}{c} \text{R}^3 \\ | \\ \text{R} \quad \text{O} \quad \text{R}^1 \quad \text{C}=\text{O} \\ | \quad || \quad | \quad / \\ \text{CH}_2=\text{C}-\text{C}-\text{N}-\text{CH}_2-\text{CH} \\ \backslash \\ \text{C}=\text{O} \\ | \\ \text{R}^2 \end{array} \quad (IV)$$

where R, R$^1$, R$^2$ and R$^3$ have the meanings stated above for the formulae (II) and (III), and (2) condensing the said 2-[(meth)acrylamidomethyl]-1,3-diketone of the formula IV with a hydrazine or hydroxylamine, thereby obtaining a 4-[(meth)acrylamidomethyl]-pyrazole or -isoxazole of the formula (I)

$$\begin{array}{c} \text{R}^3 \\ | \\ \text{R} \quad \text{O} \quad \text{R}^1 \quad \text{C} \\ | \quad || \quad | \quad // \quad \backslash \\ \text{CH}_2=\text{C}-\text{C}-\text{N}-\text{CH}_2-\text{C} \quad \quad \text{X} \\ \backslash \quad / \\ \text{C}=\text{N} \\ | \\ \text{R}^2 \end{array} \quad (I)$$

where R, R$^1$, R$^2$, R$^3$ and X independently of one another have the following meanings: R is hydrogen or methyl, R$^1$ is hydrogen, methyl or ethyl, R$^2$ and R$^3$ may be identical or different and are each alkyl of 1 to 6 carbon atoms or unsubstituted or methyl, t-butyl or phenyl substituted aryl of 6 to 20 carbon atoms and X is oxygen or an NR$^4$ group, where R$^4$ is hydrogen or a radical having the meanings of R$^2$ or R$^3$.

5. A process as claimed in claim 4, wherein, in the formulae (I), (II), (III) and (IV), R and R$^1$ are each hydrogen and R$^2$ and R$^3$ are each methyl or phenyl.

6. A process as claimed in claim 4, wherein in the second step, a 2-[(meth)acrylamidomethyl]-1,3-diketone of the formula (IV) is condensed with a hydrazinium salt or a hydrazine of the formula (V)

$$\text{NH}_2-\text{NH}-\text{R}^4 \quad (V)$$

where R$^4$ is hydrogen or a radical having the meanings of R$^2$ or R$^3$.

7. A process as claimed in claim 4, wherein, in the second step, a 2-[(meth)acrylamidomethyl]-1,3-diketone of the formula (IV) is condensed with hydroxylamine or a hydroxylammonium salt.

8. A process for the preparation of a 4-[(meth)-acrylamidomethyl]-pyrazole or -isoxazole, comprising the following steps:

(1) condensing a 1,3-diketone of the formula (II)

$$\begin{array}{c} \text{O} \quad \quad \text{O} \\ || \quad \quad || \\ \text{R}^2-\text{C}-\text{CH}_2-\text{C}-\text{R}^3 \end{array} \quad (II)$$

where R$^2$ and R$^3$ may be identical or different and independently of one another are each alkyl of 1 to 6 carbon atoms or unsubstituted or methyl, t-butyl or phenyl substituted aryl of 6 to 20 carbon atoms, with an equimolar amount of an N-methylol(meth)acrylamide of the formula III $$\begin{array}{c} \text{R} \quad \text{O} \quad \text{R}^1 \\ | \quad || \quad | \\ \text{CH}_2=\text{C}-\text{C}-\text{N}-\text{CH}_2\text{OH} \end{array} \quad (III)$$

where R is hydrogen or methyl and R$^1$ is hydrogen, methyl or ethyl, in 2 to 20 times the weight of the 1,3-diketone of the general formula (II) of a strong acid as a reaction medium at from 15° to 40° C. for a time period of from 1 to 48 hours, thereby obtaining a 2-[(meth)acrylamidomethyl]-1,3-diketone of the formula (IV)

$$\begin{array}{c} \text{R}^3 \\ | \\ \text{R} \quad \text{O} \quad \text{R}^1 \quad \text{C}=\text{O} \\ | \quad || \quad | \quad / \\ \text{CH}_2=\text{C}-\text{C}-\text{N}-\text{CH}_2-\text{CH} \\ \backslash \\ \text{C}=\text{O} \\ | \\ \text{R}^2 \end{array} \quad (IV)$$

where R, R$^1$, R$^2$ and R$^3$ have the meanings stated above for the formulae (II) and (III), (2) isolating the said 2-[(meth)acrylamidomethyl]-1,3-diketone of the formula IV by pouring the reaction mixture obtained from process step 1 on a large excess of ice, thus precipitating the said 2-[(meth)acrylamidomethyl]-1,3-diketone, and (3) condensing the said 2-[(meth)acrylamidomethyl]-1,3-diketone of the formula IV with an equimolar amount of a hydrazine or hydroxylamine in an aqueous reaction medium at the boiling point of said medium, thereby obtaining a 4-[(meth)acrylamidomethyl]-pyrazole or -isoxazole of the formula (I)

$$\begin{array}{c} \text{R}^3 \\ | \\ \text{R} \quad \text{O} \quad \text{R}^1 \quad \text{C} \\ | \quad || \quad | \quad // \quad \backslash \\ \text{CH}_2=\text{C}-\text{C}-\text{N}-\text{CH}_2-\text{C} \quad \quad \text{X} \\ \backslash \quad / \\ \text{C}=\text{N} \\ | \\ \text{R}^2 \end{array} \quad (I)$$

where R, R$^1$, R$^2$, R$^3$ and X independently of one another have the following meanings: R is hydrogen or methyl, R$^1$ is hydrogen, methyl or ethyl, R$^2$ and R$^3$ may be identical or different and are each alkyl of 1 to 6 carbon atoms or unsubstituted or substituted aryl of 6 to 20 carbon atoms and X is oxygen or an NR$^4$ group, R$^4$ is hydrogen or a radical having the meanings of R$^2$ or R$^3$.

\* \* \* \* \*